(12) United States Patent
Park et al.

(10) Patent No.: US 11,517,206 B2
(45) Date of Patent: *Dec. 6, 2022

(54) ELECTRONIC DEVICE, BLOOD PRESSURE MEASUREMENT METHOD OF ELECTRONIC DEVICE AND BLOOD PRESSURE MEASUREMENT SYSTEM

(71) Applicant: SAMSUNG ELECTRONICS CO., LTD., Suwon-si (KR)

(72) Inventors: Sang Yun Park, Hwaseong-si (KR); Jae Min Kang, Seoul (KR); Yong Joo Kwon, Yongin-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 689 days.

This patent is subject to a terminal disclaimer.

(21) Appl. No.: 16/419,099

(22) Filed: May 22, 2019

(65) Prior Publication Data

US 2019/0357779 A1 Nov. 28, 2019

(30) Foreign Application Priority Data

May 25, 2018 (KR) ........................ 10-2018-0059927

(51) Int. Cl.
*A61B 5/00* (2006.01)
*A61B 5/021* (2006.01)
(Continued)

(52) U.S. Cl.
CPC ........ *A61B 5/02108* (2013.01); *A61B 5/0002* (2013.01); *A61B 5/0077* (2013.01);
(Continued)

(58) Field of Classification Search
None
See application file for complete search history.

(56) References Cited

U.S. PATENT DOCUMENTS

| 7,181,975 B1* | 2/2007 | Bradley ............... G01L 9/0072 |
| | | 73/718 |
| 8,761,853 B2 | 6/2014 | Thaveeprungsriporn et al. |

(Continued)

FOREIGN PATENT DOCUMENTS

| JP | 7-194562 | 8/1995 |
| JP | 2008-183257 A | 8/2008 |

(Continued)

OTHER PUBLICATIONS

Dictionary.com. (2022). Communication interface definition and meaning. Dictionary.com. Retrieved Feb. 7, 2022, from www.dictionary.com/browse/communication-interface (Year: 2022).*

*Primary Examiner* — Allen Porter
*Assistant Examiner* — Samuel C Kim
(74) *Attorney, Agent, or Firm* — Sughrue Mion, PLLC

(57) ABSTRACT

According to one aspect of the present disclosure, an electronic device may include: a communication interface configured to receive, from a touch pen, force information about a force of the touch pen exerted onto an object when the object is in contact with the touch pen; a pulse wave measurer configured to measure a pulse wave of the object when the object is brought into contact with the electronic device by the force of the touch pen; and a processor configured to estimate a blood pressure of the object based on the force information and the pulse wave.

22 Claims, 12 Drawing Sheets

(51) Int. Cl.
*A61B 5/022* (2006.01)
*A61B 5/0522* (2021.01)
*A61B 5/1171* (2016.01)
*G06V 40/18* (2022.01)

(52) U.S. Cl.
CPC ........ *A61B 5/02241* (2013.01); *A61B 5/0522* (2013.01); *A61B 5/1176* (2013.01); *A61B 5/6897* (2013.01); *G06V 40/18* (2022.01)

(56) References Cited

U.S. PATENT DOCUMENTS

| | | | | |
|---|---|---|---|---|
| 11,344,209 | B2* | 5/2022 | Park | A61B 5/02108 |
| 2006/0009700 | A1* | 1/2006 | Brumfield | A61B 5/6838 |
| | | | | 600/587 |
| 2007/0106172 | A1* | 5/2007 | Abreu | A61P 7/02 |
| | | | | 600/549 |
| 2010/0076398 | A1* | 3/2010 | Scheurer | A61B 5/0215 |
| | | | | 600/483 |
| 2015/0062078 | A1* | 3/2015 | Christman | A61B 5/6897 |
| | | | | 345/174 |
| 2015/0374248 | A1* | 12/2015 | Hu | A61B 5/02225 |
| | | | | 600/491 |
| 2016/0374557 | A1 | 12/2016 | Bakhshi et al. | |
| 2017/0180988 | A1 | 6/2017 | Kim et al. | |
| 2019/0008399 | A1* | 1/2019 | Mukkamala | A61B 5/02225 |
| 2019/0298224 | A1* | 10/2019 | Rahman | A61B 5/0816 |
| 2019/0313918 | A1* | 10/2019 | Li | A61B 5/0245 |
| 2020/0288995 | A1* | 9/2020 | Hwang | A61B 5/02007 |
| 2020/0383641 | A1* | 12/2020 | Hwang | A61B 5/7278 |
| 2021/0022622 | A1* | 1/2021 | Lee | G06V 40/67 |

FOREIGN PATENT DOCUMENTS

| | | |
|---|---|---|
| KR | 10-0650044 B1 | 11/2006 |
| KR | 10-2014-0076852 A | 6/2014 |
| KR | 10-1448135 B1 | 10/2014 |
| KR | 10-2016-0109250 A | 9/2016 |
| WO | WO-2017152098 A1 * 9/2017 ......... A61B 5/02141 |

* cited by examiner

ELECTRONIC DEVICE, BLOOD PRESSURE MEASUREMENT METHOD OF ELECTRONIC DEVICE AND BLOOD PRESSURE MEASUREMENT SYSTEM

CROSS-REFERENCE TO RELATED APPLICATION(S)

This application is based on and claims the benefit under 35 USC § 119(a) to Korean Patent Application No. 10-2018-0059927, filed on May 25, 2018, in the Korean Intellectual Property Office, the disclosure of which is incorporated herein by reference in its entirety.

BACKGROUND

1. Field

The following description relates to a technology for measuring a blood pressure in a cuffless manner.

2. Description of Related Art

A pressurized cuff-based method is used for general blood pressure measurement. The pressurized cuff-based method is a non-continuous measurement method in which a cuff is used to tighten blood vessels up to the maximum blood pressure and loosen to measure a blood pressure. The pressurized cuff-based method is difficult to apply to a portable device due to the configuration of a pressurizing pump or the like.

Recently, a blood pressure measurement apparatus employing non-pressurized cuffless method for measuring a blood pressure without using a cuff has been studied. For example, there are a pulse transit time (PTT)-based blood pressure measurement apparatus and method and a pulse wave analysis (PWA)-based blood pressure measurement apparatus and method. The PTT method is disadvantageous in that it is necessary to perform correction for each individual for accurate measurement and it is difficult to construct a compact device because bio-signals must be measured at two or more positions in order to measure the pulse wave velocity. Because the PWA method estimates a blood pressure only by analyzing the pulse wave form, it is disadvantageously vulnerable to noise and has a limitation in accurate blood pressure measurement.

SUMMARY

This summary is provided to introduce a selection of concepts in a simplified form that are further described below in the Detailed Description.

The following description relates to an apparatus and method for measuring more accurate blood pressure in a cuffless manner by using an existing sensor provided in an electronic device.

In an aspect of the present disclosure, there is provided an electronic device including: a communication interface configured to receive, from a touch pen, force information about a force of the touch pen exerted onto an object when the object is in contact with the touch pen; a pulse wave measurer configured to measure a pulse wave of the object when the object is brought into contact with the electronic device by the force of the touch pen; and a processor configured to estimate a blood pressure of the object based on the force information and the pulse wave.

The electronic device may further include a sensor module including at least one of a face recognition sensor, a pulse wave sensor, a camera, an illuminance sensor, and an iris recognition sensor. The pulse wave measurer may be further configured to measure the pulse wave of the object when the object is brought into contact with the sensor module The pulse wave measurer may measure the pulse wave of the object by using at least one of natural light, a display of the electronic device, a light source of the touch pen, or a flash the electronic device, as a light source, and by using the at least one of the face recognition sensor, the camera, the illuminance sensor, and the iris recognition sensor, as a light receiver.

The pulse wave sensor may include a light source configured to emit light to the object and a light receiver configured to receive light reflected or scattered from the object.

The communication interface may receive the force information from the touch pen using an electromagnetic induction method.

The communication interface may receive the force information from the touch pen using one of Bluetooth communication, Bluetooth low energy (BLE) communication, near field communication (NFC), wireless local access network (WLAN) communication, ZigBee communication, infrared data association (IrDA) communication, Wi-Fi direct (WFD) communication, ultra-wideband (UWB) communication, Ant+ communication, Wi-Fi communication, radio frequency identification (RFID) communication, third generation (3G) communication, fourth generation (4G) communication, and fifth generation (5G) communication.

The processor may calculate a contact pressure between the object and the electronic device, which is caused by the force of the touch pen pressing the object, based on the force information, and may estimate the blood pressure of the object using the contact pressure and the pulse wave.

The processor may calculate the contact pressure between the object and the electronic device based on the force information and pre-stored contact area information indicating a contact area between the object and the electronic device.

The pre-stored contact area information may be a default value or a value measured in advance according to a predetermined contact area measurement process.

The predetermined contact area measurement process may include measuring the contact area when the object is brought into contact with a display screen of the electronic device.

The electronic device may further include a power supply configured to supply power to the touch pen using an electromagnetic induction method.

The object may be a body part of a user of the electronic device. The processor may generate guide information for measuring the pulse wave of the object using the touch pen and provide the guide information to the user.

The guide information may include at least one of action guide information to guide the user to press the object against the electronic device by using the touch pen and pressure guide information to guide change in contact pressure between the object and the electronic device which is caused by the force of the touch pen pressing the object.

The processor may provide the guide information through a display of the electronic device or through another electronic device.

In another aspect of the present disclosure, there is provided a blood pressure measurement method of an electronic device, including: receiving, from a touch pen, force information about a force of the touch pen exerted onto an object when the object is in contact with the touch pen; measuring a pulse wave of the object when the object is brought into contact with the electronic device by the force of the touch pen; and estimating a blood pressure of the object based on the force information and the pulse wave.

The measuring the pulse wave of the object may include measuring the pulse wave by a sensor module including a pulse wave sensor, and at least one of a face recognition sensor, a camera, an illuminance sensor, and an iris recognition sensor.

The measuring the pulse wave of the object may include measuring the pulse wave of the object by using natural light, a display of the electronic device, a light source of the touch pen, or a flash of the electronic device, as a light source, and by using at least one of the face recognition sensor, the camera, the illuminance sensor, and the iris recognition sensor as a light receiver.

The estimating the blood pressure of the object may include calculating a contact pressure between the object and the electronic device, which is caused by the force of the touch pen pressing the object, based on the force information, and estimating the blood pressure of the object based on the contact pressure and the pulse wave.

The calculating the contact pressure may include calculating the contact pressure between the object and the electronic device based on the force information and pre-stored contact area information indicating a contact area between the object and the electronic device.

The pre-stored contact area may be a default value or a value measured in advance according to a predetermined contact area measurement process.

The object may be a body part of a user of the electronic device. The blood pressure measurement method may further include generating action guide information to guide the user to press the object against the electronic device by using the touch pen and providing the action guide information to the user.

The blood pressure measurement method may further include generating pressure guide information to guide change in contact pressure between the object and the electronic device, which is caused by the force of the touch pen pressing the object.

Other features and aspects will be apparent from the following detailed description, the drawings, and the claims.

Figure 1:
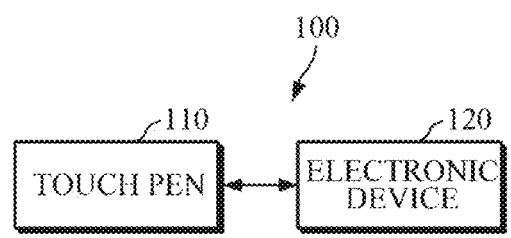
FIG. 1 is a block diagram illustrating a blood pressure measurement system according to one embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It should be noted that in some alternative implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved.

Terms described in below are selected by considering functions in the embodiment and meanings may vary depending on, for example, a user or operator's intentions or customs. Therefore, in the following embodiments, when terms are specifically defined, the meanings of terms should be interpreted based on definitions, and otherwise, should be interpreted based on general meanings recognized by those skilled in the art.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising," will be understood to imply the inclusion of stated elements but not the exclusion of any other elements. Terms such as ". . . unit" and "module" denote units that process at least one function or operation, and they may be implemented by using hardware, software, or a combination of hardware and software.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

It will also be understood that the elements or components in the following description are discriminated in accordance with their respective main functions. In other words, two or more elements may be made into one element or one element may be divided into two or more elements in accordance with a subdivided function. Additionally, each of the elements in the following description may perform a part or whole of the function of another element as well as its main function, and some of the main functions of each of the elements may be performed exclusively by other elements. Each element may be realized in the form of a hardware component, a software component, and/or a combination thereof.

FIG. 1 is a block diagram illustrating a blood pressure measurement system according to one embodiment.

Referring to FIG. 1, the blood pressure measurement system may include a touch pen 110 and an electronic device 120.

The touch pen 110 is a device which inputs data to the electronic device 120 by touching a screen of the electronic device 120 and may be variously called an electronic pen, a stylus, a stylus pen, a smart pen, or the like. The electronic device 120 is a device capable of performing various functions by receiving a touch-based input and may include a mobile phone, a smartphone, a tablet computer, a notebook computer, a personal digital assistant (PDA), a portable multimedia player (PMP), a navigation system, an MP3 player, a digital camera, a wearable device, and the like, and the wearable device may include a wearable device of wristwatch-type, wrist band type, ring type, ankle band type, thigh band type, forearm type, etc. However, the electronic device 120 is not limited to the above examples and the wearable device is also not limited to the above examples.

The touch pen 110 and the electronic device 120 may be implemented as at least one of an electromagnetic induction type, an active electrostatic type, a resistive type and a capacitive type.

The electromagnetic induction type is operated by electromagnetic induction by which an electromagnetic field radiating from a coil embedded in the touch pen 110 and an electromagnetic field radiating from a coil embedded in the electronic device 102 recognize each other. In the electromagnetic induction type, the electronic device 120 supplies power to the touch pen 110 through an electromagnetic field, and hence the touch pen 110 may not need to be provided with a separate power source. In addition, the touch pen 110 may determine a position, a pen pressure, or the like of the touch pen 110 by transmitting a specific signal to the electronic device 120 through an electromagnetic field and receiving a specific signal from the touch pen 110 of the electronic device 120 through the electromagnetic field.

Unlike the electromagnetic induction type, the active electrostatic type is operated by detecting, by the electronic device 120, an electrostatic signal transmitted from the touch pen 110. In the active electrostatic type, the touch pen 110 may transmit an electrostatic signal, and thus is provided with a separate power source.

The resistive type is operated by detecting a pressure applied to a screen of the electronic device 120, and the capacitive type uses a change in electric signal and is operated by detecting a change in amplitude of capacitance of a screen of the electronic device 120.

The electronic device 120 may calculate a contact pressure between an object of interest and the electronic device 120 which is caused by a force of the touch pen 110 pressing the object of interest. When the object of interest is brought into contact with the electronic device 120 and pressed against the electronic device 120 by the force of the touch pen 110 pressing the object, the electronic device 120 may measure a pulse wave of the object of interest and estimate a blood pressure of the object based on the measured pulse wave and the calculated contact pressure.

Figure 2:
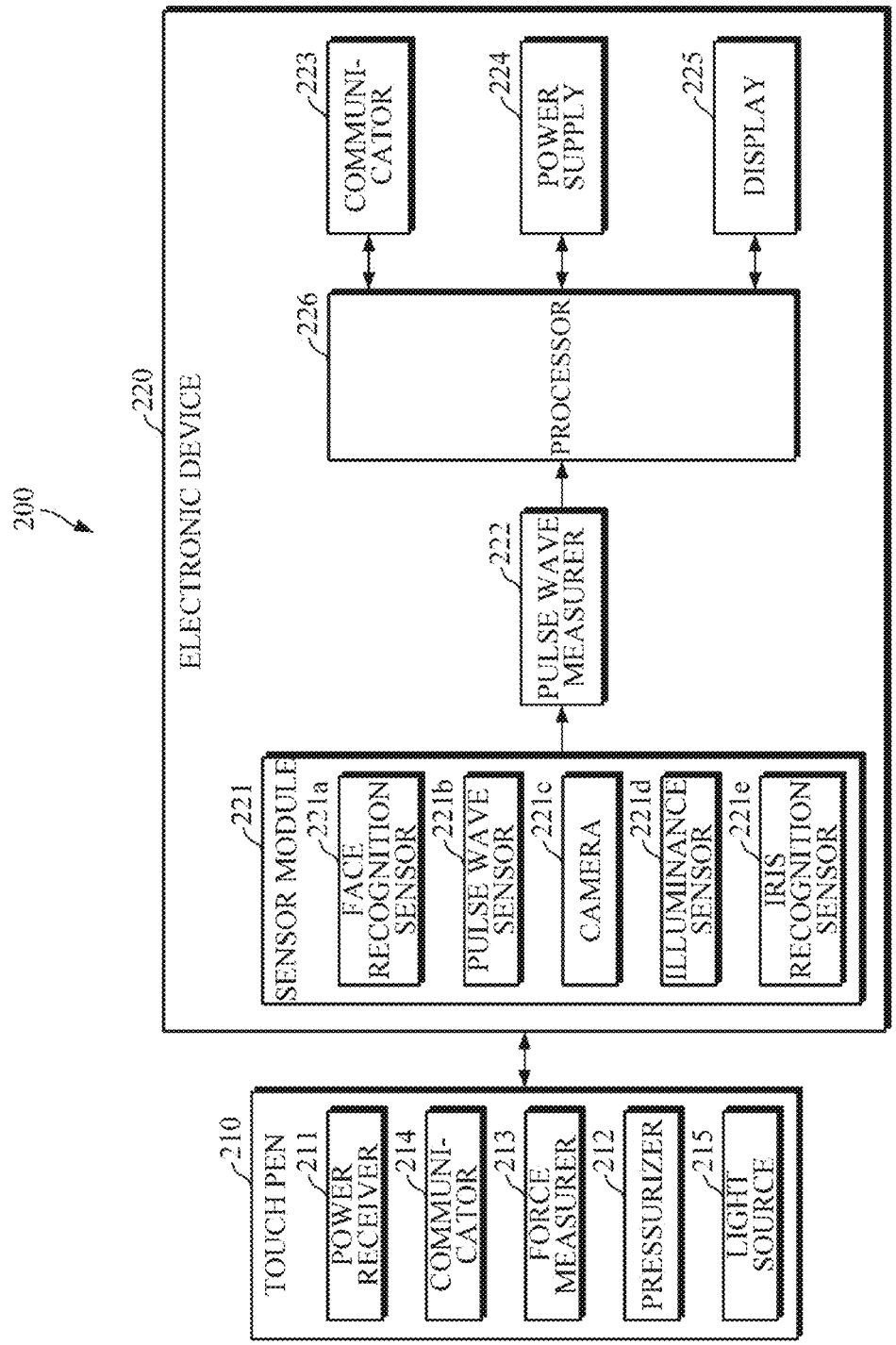
FIG. 2 is a diagram illustrating a blood pressure measurement system implemented as an electromagnetic induction type according to one embodiment.

FIG. 2 is a diagram illustrating a blood pressure measurement system implemented as an electromagnetic induction type according to one embodiment. The blood pressure measurement system 200 of FIG. 2 may be one embodiment of the blood pressure measurement system 100 of FIG. 1. The blood pressure measurement system 200 of FIG. 2 is implemented as an electromagnetic induction type, and thus a touch pen 210 and an electronic device may each include a coil for electromagnetic induction. However, for convenience of illustration, the coils are omitted in FIG. 2.

Referring to FIG. 2, the blood pressure measurement system 200 implemented as an electromagnetic induction type may include the touch pen 210 and the electronic device 220.

The touch pen 210 may include a power receiver 211, a pressurizer 212, a force measurer (e.g., a force sensor) 213, and a communicator (e.g., a communication interface) 214.

The power receiver 211 may receive power from the electronic device 220 through an electromagnetic field by an electromagnetic induction method.

The pressurizer 212 may be a part which can be in contact with the electronic device 220 or an object of interest and may protrude from one end of the touch pen 210. The pressurizer 212 may be referred to as a tip or a pen point.

The force measurer 213 may measure a force applied to the pressurizer 212. For example, the force measurer 213 may measure a force of the pressurizer 212 pressing the object of interest. To this end, the pressurizer 212 may be connected to the force measurer 213 and may transmit the force applied to the pressurizer 212 to the force measurer 213.

The communicator 213 may communicate with the electronic device 220 through an electromagnetic field. For example, the communicator 214 may transmit force information measured by the force measurer 213 to the electronic device 220 through an electromagnetic field.

Meanwhile, according to one embodiment, the touch pen 210 may further include a light source 215 to be used for measuring a pulse wave of the object of interest. The light source 215 may emit visible light, near infrared ray (NIR) light, or mid-infrared ray (MIR) light to the object of interest. However, a wavelength of light to be emitted from the light source may vary according to the measurement purpose or a component to be analyzed. In addition, the light source is not necessarily formed as a single light emitting body and may be formed as an array of a plurality of light emitting bodies.

The electronic device 220 may include a sensor module 221, a pulse wave measurer (e.g., an optical sensor, a spectrometer, a photoplethysmogram sensor, an electrocardiography, etc.) 222, a communicator (e.g., a communication interface) 223, a power supply 224, a display 225, and a processor 226.

The sensor module 221 may measure a physical amount or sense an operational state of the electronic device 220 and convert the measured or sensed information into an electric signal. The sensor module 220 may include at least one of a face recognition sensor 221a, a pulse wave sensor 221b, a camera 221c, an illuminance sensor 221d, and an iris recognition sensor 221e. The sensor module 221 may further include a control circuit for controlling at least one sensor included in the sensor module 221. According to one embodiment, the electronic device 220 may further include a processor formed as a part of the processor 226 or formed separately from the processor 226 to control the sensor module 221, and may control the sensor module 221 using the processor when the processor 226 is in a sleep mode.

The pulse wave measurer 222 may measure a pulse wave of the object of interest using the sensor module 221 when the object is brought into contact with the sensor module 221 by the force of the touch pen 210 pressing the object. For example, the pulse wave measurer 222 may measure the pulse wave of the object using the pulse wave sensor 221*b* including a light source and a light receiver. In another example, the pulse wave measurer 222 may use natural light, a part or the whole of the display 225, the light source 215 of the touch pen 210, or the flash of the camera 221*c* as the light source and use one of the face recognition sensor 221*a*, the camera 221*c*, the illuminance sensor 221*d*, and the iris recognition sensor 221*e* as the light receiver to measure the pulse wave of the object of interest.

The communicator 223 may communicate with the touch pen 210 through an electromagnetic field. For example, the communicator 223 may receive the force information measured by the force measurer 213 of the touch pen 210, that is, the force information about the force of the pressurizer 212 of the touch pen 210 pressing the object, from the touch pen 210 through an electromagnetic field using an electromagnetic induction method.

In addition, the communicator 223 may communicate with an external device using various communication technologies, such as Bluetooth communication, Bluetooth low energy (BLE) communication, near field communication (NFC), wireless local access network (WLAN) communication, ZigBee communication, infrared data association (IrDA) communication, Wi-Fi direct (WFD) communication, ultra-wideband (UWB) communication, Ant+ communication, Wi-Fi communication, radio frequency identification (RFID) communication, 3rd generation (3G) communication, 4G communication, and 5G communication. In this case, the external device may be medical equipment using data dealt by the electronic device 220 or the processing result data of the electronic device 220, or a printer or a display for outputting a result. In addition, the external device may be, but not limited to, a digital TV, a desktop computer, a mobile phone, a smartphone, a tablet computer, a notebook computer, a PDA, a PMP, a navigation system, an MP3 player, a digital camera, a wearable device, and the like.

The power supply 224 may supply power to the touch pen 210 through an electromagnetic field using an electromagnetic induction method.

The display 225 may display the data dealt by the electronic device 220 or the processing result data of the electronic device 220. According to one embodiment, the display 225 may be implemented as a touch screen.

The processor 226 may control an overall operation of the electronic device 220.

Periodically or upon the occurrence of a specific event, such as a user command, the processor 226 may generate guide information for measuring a pulse wave of the object using the touch pen 210 and may provide the guide information to the user through an output means. In particular, the output means may include a visual output means (e.g., a display), an audio output means (e.g., a speaker), a tactile output means (e.g., a vibrator, or a haptic motor), and the like. According to one embodiment, the guide information may include action guide information to guide a user's action to measure a pulse wave of the object of interest by applying a force to the object using the touch pen 210 and pressure guide information to guide change in contact pressure between the object and the electronic device 220, which is caused by the force of the touch pen 210 pressing the object.

The processor 226 may measure a pulse wave of the object by controlling the pulse wave measurer 222 when the object is brought into contact with the sensor module 221 by the force of the touch pen 210 pressing the object.

In addition, the processor 226 may calculate a contact pressure between the object and the sensor module 221, which is caused by the force of the touch pen 210 pressing the object based on the force information received from the touch pen 210. When the object of interest is brought into contact with the sensor module 221 as the touch pen 210 presses the object, the force of the touch pen 210 pressing the object may be transmitted to the sensor module 221 through the object. Therefore, according to one embodiment, the processor 226 may use the force information received from the touch pen 210, that is, the force information about the force of the pressurizer 212 of the touch pen 210 pressing the object, as contact force information between the object and the sensor module 221 and calculate the contact pressure between the object and the sensor module 221 based on the force information and pre-stored contact area information. The pre-stored contact area information may be a default value or a value measured in advance according to a predetermined process of measuring the contact area prior to the measurement of the pulse wave of the object and may be stored in an internal or external memory. The memory may include at least one type of memory, such as flash memory, hard disk type memory, multimedia card micro type memory, card-type memory (e.g., SD or XD memory), random access memory (RAM), static random access memory (SRAM), read only memory (ROM), electrically erasable programmable read only memory (EEPROM), programmable read only memory (PROM), magnetic memory, magnetic disk, optical disk, and the like.

The processor 226 may estimate a blood pressure of the object based on the pulse wave of the object and the contact pressure between the object and the sensor module 221. For example, the processor 226 may estimate a blood pressure of the user by analyzing the change in pulse wave in accordance with the change in contact pressure.

The blood pressure may include a diastolic blood pressure (DBP), a systolic blood pressure (SBP), and a mean arterial pressure (MAP), and the contact pressure applied to the user's finger may act as an external pressure applied to the blood vessel. When the contact pressure becomes smaller than the MAP, an elastic restoring force of tissue acts in a direction of compressing the blood vessel and hence the amplitude of the pulse wave becomes small. When the contact pressure is equal to the MAP, the elastic restoring force of tissue becomes zero and hence does not affect the blood vessel so that the amplitude of the pulse wave is maximized. In addition, when the contact pressure becomes greater than the MAP, the elastic restoring force of tissue acts in a direction of expanding the blood vessel and hence the amplitude of the pulse wave becomes smaller. Therefore, the processor 226 may analyze the change in pulse wave in accordance with the change in contact pressure and estimate the MAP using the contact pressure at a point where the amplitude of the pulse wave is maximized. In addition, the processor 226 may estimate the SBP using a measured contact pressure, at a point where a ratio of an amplitude of the pulse wave to a predetermined maximum amplitude is a first ratio (e.g., 0.6), and may estimate the DBP using the measured contact pressure, at a point where the ratio of the amplitude of the pulse wave to the predetermined maximum amplitude is a second ratio (e.g. 0.7).

Figure 3:
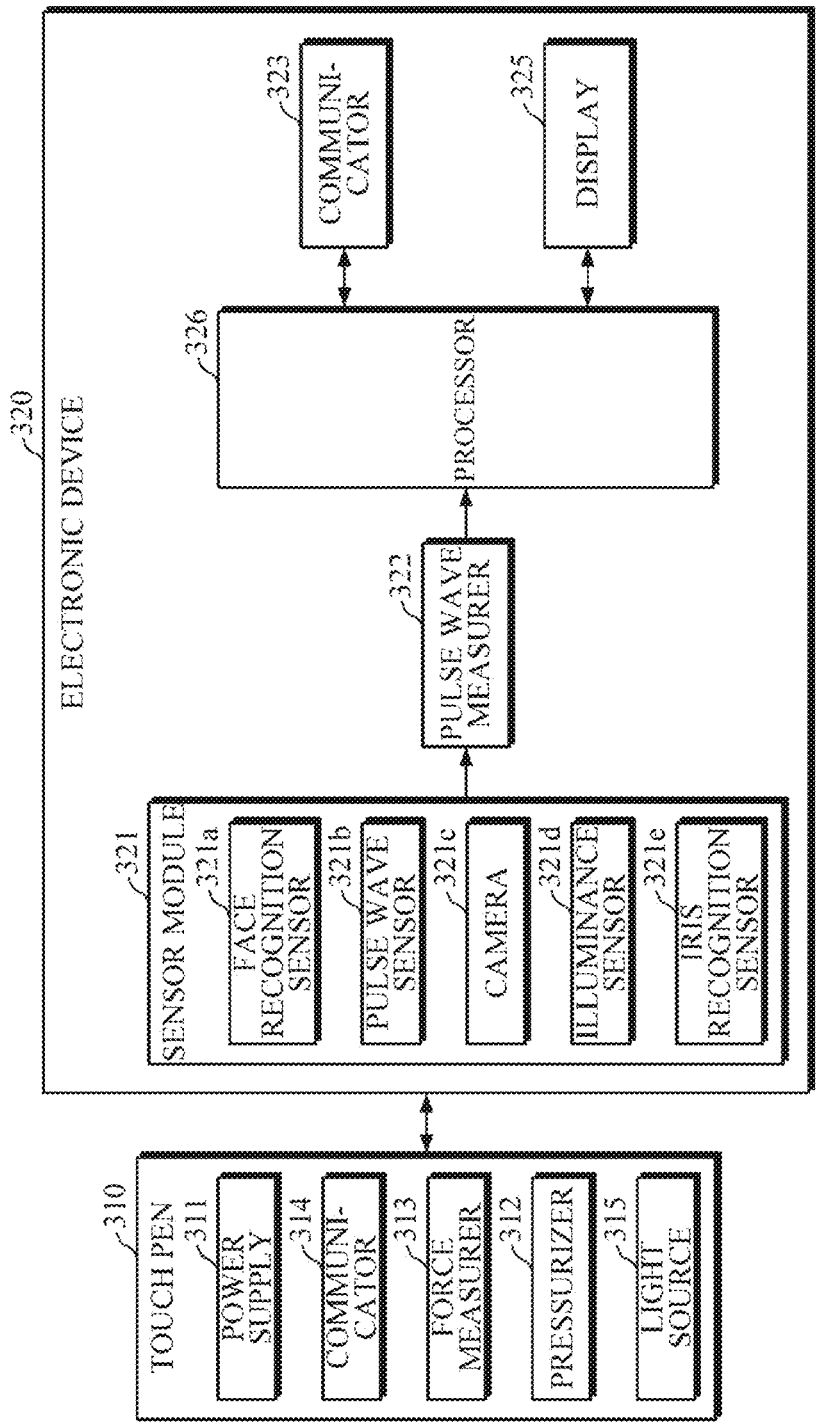
FIG. 3 is a diagram illustrating a blood pressure measurement system implemented as an active electrostatic type according to one embodiment.

FIG. 3 is a diagram illustrating a blood pressure measurement system implemented as an active electrostatic type according to one embodiment. The blood pressure measurement system 300 of FIG. 3 may be one embodiment of the blood pressure measurement system 100 of FIG. 1.

Referring to FIG. 3, the blood pressure measurement system 300 implemented as an active electrostatic type may include a touch pen 310 and an electronic device 320.

The touch pen 310 may include a power supply 311, a pressurizer 312, a force measurer (e.g., a force sensor) 313, and a communicator (e.g., a communication interface) 314. In this case, the pressurizer 312 and the force measurer 313 may operate substantially the same as the pressurizer 212 and the force measurer 213 of FIG. 2, respectively, and thus detailed descriptions thereof will not be reiterated.

The power supply 311 may be provided for operation of the touch pen 310 and may supply power to the touch pen 310.

The communicator 314 may communicate with the electronic device 320 using various communication technologies, such as Bluetooth communication, BLE communication, NFC, WLAN communication, ZigBee communication, IrDA communication, WFD communication, UWB communication, Ant+ communication, Wi-Fi communication, RFID communication, 3G communication, 4G communication, and 5G communication. For example, the communicator 314 may transmit force information measured by the force measurer 313 to the electronic device 320 using the various aforementioned communication technologies.

Meanwhile, according to one embodiment, the touch pen 310 may further include a light source 315 to be used for measuring a pulse wave of the object of interest. Here, the light source 315 may operate substantially the same as the light source 215 of FIG. 2, and thus detailed description thereof will not be reiterated.

The electronic device 320 may include a sensor module 321, a pulse wave measurer (e.g., an optical sensor, a spectrometer, a photoplethysmogram sensor, an electrocardiography, etc.) 322, a communicator (e.g., a communication interface) 323, a display 325, and a processor 326. Here, the sensor module 321, the pulse wave measurer 322, the display 325, and the processor 326 are substantially the same as the sensor module 221, the pulse wave measurer 222, the display 225, and the processor 226 of FIG. 2, respectively, and thus detailed descriptions thereof will not be reiterated.

The communicator 323 may communicate with the touch pen 310 and/or an external device using various communication technologies, such as Bluetooth communication, BLE communication, NFC, WLAN communication, ZigBee communication, IrDA communication, WFD communication, UWB communication, Ant+ communication, Wi-Fi communication, RFID communication, 3G communication, 4G communication, and 5G communication. For example, the communicator 323 may receive the force information, which has been measured by the force measurer 313, from the touch pen 310 using the various aforementioned communication technologies.

Figure 4:
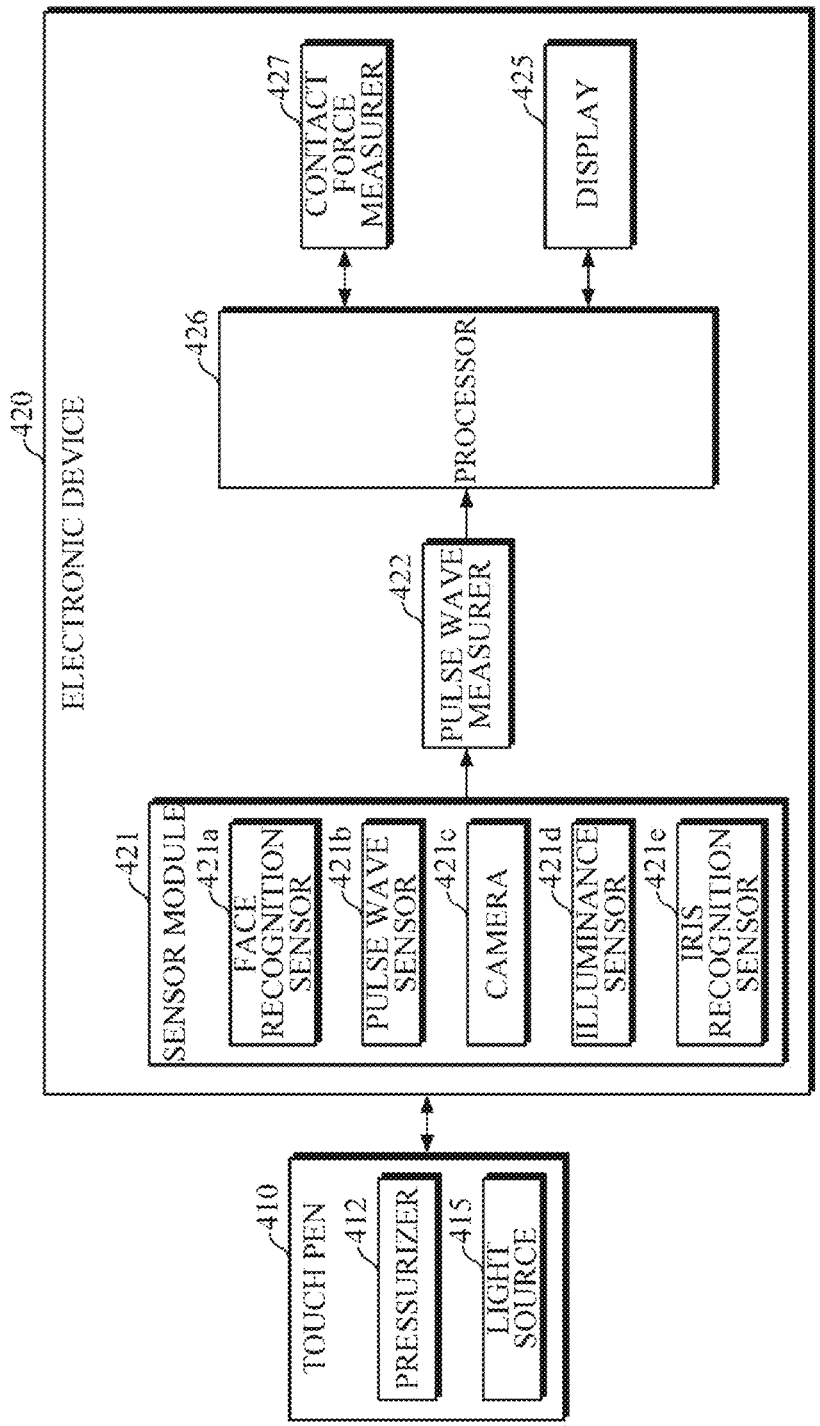
FIG. 4 is a diagram illustrating a blood pressure measurement system implemented as a resistive type or a capacitive type according to one embodiment.

FIG. 4 is a diagram illustrating a blood pressure measurement system implemented as a resistive type or a capacitive type according to one embodiment. The blood pressure measurement system 400 of FIG. 4 may be one embodiment of the blood pressure measurement system 100 of FIG. 1.

Referring to FIG. 4, the blood pressure measurement system 400 implemented as a resistive type or a capacitive type may include a touch pen 410 and an electronic device 420.

The touch pen 410 may include a pressurizer 412.

The pressurizer 412 may be a part capable of being in contact with the electronic device 320 or the object of interest and may protrude from one end of the touch pen 410. The pressurizer 412 may be referred to as a tip or a pen point.

According to one embodiment, the touch pen 410 may further include a light source 415 to be used for measuring a pulse wave of the object. Here, the light source 415 is the same as the light source 215 of FIG. 2, and thus detailed description thereof will not be reiterated.

The electronic device 420 may include a sensor module 421, a pulse wave measurer (e.g., an optical sensor, a spectrometer, a photoplethysmogram sensor, an electrocardiography, etc.) 422, the display 425, a contact force measurer (e.g., a contact force sensor) 427, and a processor 426. Here, the sensor module 421, the pulse wave measurer 422, and the display 425 are substantially the same as the sensor module 221, the pulse wave measurer 222, and the display 225 of FIG. 2, respectively, and thus detailed descriptions thereof will not be reiterated.

The contact force measurer 427 may measure a contact force between the object of interest and the sensor module 421 which is caused by a force of the pressurizer 412 pressing the object. To this end, the contact force measurer 427 may include a force sensor and the like. According to one embodiment, the contact force measurer 427 may be disposed below the sensor module 421 used in measuring a pulse wave.

The processor 426 may control an overall operation of the electronic device 420.

Periodically or upon the occurrence of a specific event, such as a user command, the processor 426 may generate guide information for measuring a pulse wave of the object using the touch pen 410 and may provide the guide information to the user through an output means.

When the object is brought into contact with the sensor module 421 by the force of the touch pen 410 pressing the object, the processor 426 may measure a pulse wave of the object by controlling the pulse wave measurer 422 and calculate the contact pressure between the object and the electronic device 420 based on the contact force information measured by the contact force measurer 427 and pre-stored contact area information.

In addition, the processor 426 may estimate a blood pressure of the object based on the pulse wave of the object and the contact pressure between the object and the sensor module 421.

Figure 5:
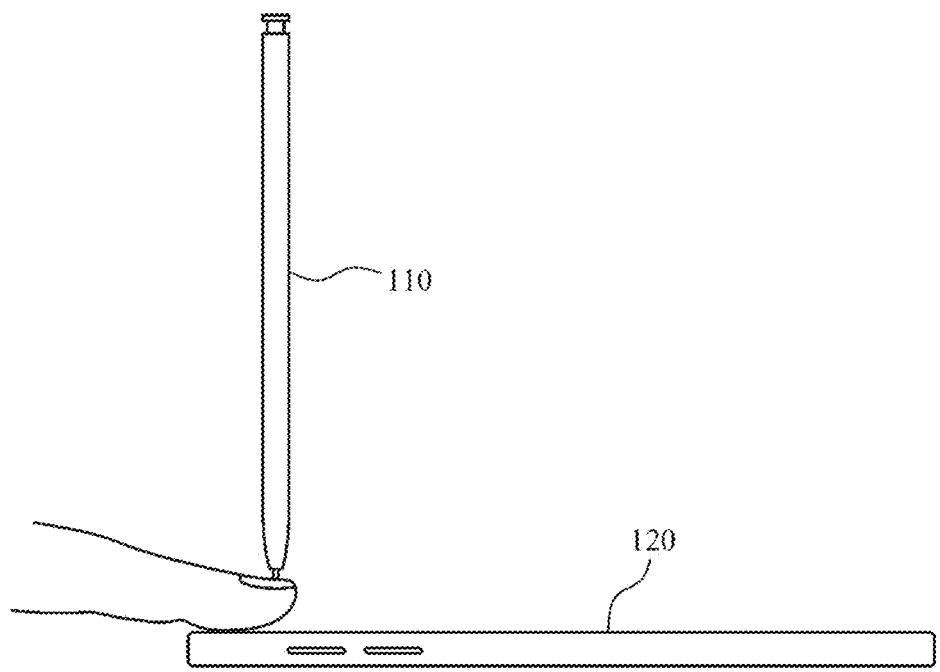
FIG. 5 is a diagram illustrating a method of pressing an object of interest using a touch pen.

FIG. 5 is a diagram illustrating a method of pressing an object of interest using a touch pen.

Referring to FIG. 5, the user places the touch pen 110 vertically on a nail of a finger and presses the user's finger vertically with the touch pen 110 to bring the user's finger in contact with the sensor module of the electronic device 120. In this case, a contact pressure of the finger and the electronic device 120 may vary according to a force of the touch pen 110 pressing the user's finger.

Figure 6:
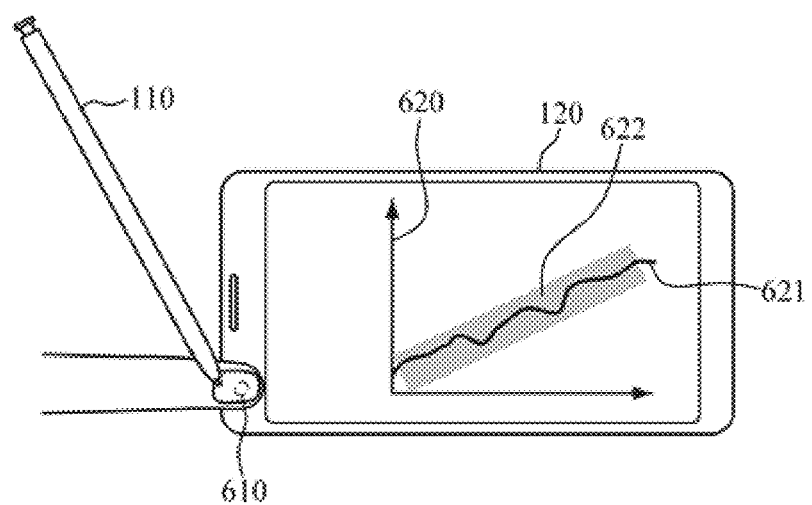
FIG. 6 is a diagram illustrating an example of measuring a blood pressure using natural light as a light source.

FIG. 6 is a diagram illustrating an example of measuring a blood pressure using natural light as a light source.

Referring to FIG. 6, the user places a finger above a sensor module 610 (e.g., a face recognition sensor, a camera, an illuminance sensor, and an iris recognition sensor) of an electronic device 120, places the touch pen 110 vertically above a nail, and then presses the nail in a direction perpendicular to the electronic device 120. In particular, the electronic device 120 may provide action guide information to guide the user's action to press the nail using the touch pen 110 to the user through a display screen.

The touch pen 110 may measure a force applied to the nail by the touch pen 110 and transmit measured force information to the electronic device 120.

The electronic device 120 may receive the force information from the touch pen 110 and calculate a contact pressure between the finger and the sensor module 610 based on the received force information and pre-stored contact area information. In this case, the contact area information may be a default value or a value measured in advance according to a predetermined contact area measurement process prior to measurement of the pulse wave of the user.

The electronic device 120 may generate pressure guide information 620 to guide change in contact pressure based on the calculated contact pressure and provide the generated pressure guide information 620 through a display screen. In particular, the pressure guide information 620 may include a current contact pressure 621 and a desired range 622 of contact pressure.

The electronic device 120 may measure a pulse wave of the user using the sensor module 610 of the electronic device 120. The electronic device 120 may measure the pulse wave of the user by using natural light as a light source and using the sensor module 610 of the electronic device 120 as a light receiver.

The electronic device 120 may estimate a blood pressure of the user based on the calculated contact pressure and the measured pulse wave.

Figure 7:
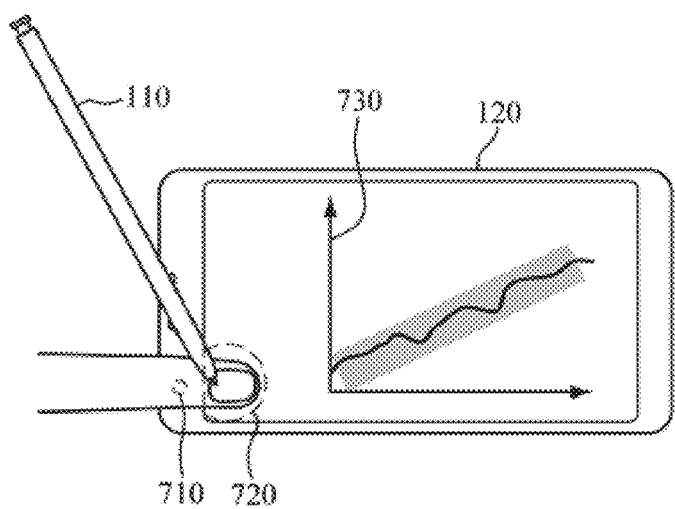
FIG. 7 is a diagram illustrating an example of measuring a blood pressure using a part of a display as a light source.

FIG. 7 is a diagram illustrating an example of measuring a blood pressure using a part of a display as a light source.

Referring to FIG. 7, a user may place his/her finger above a sensor module 710 (e.g., a face recognition sensor, a camera, an illuminance sensor, an iris recognition sensor, etc.) and a part 720 of a display of an electronic device, place a touch pen 110 vertically above the nail, and press the nail in a direction perpendicular to the electronic device 120. In this case, the electronic device 120 may provide the user with action guide information to guide a user's action to press the nail using the touch pen 110 through a display screen.

The touch pen 110 may measure a force applied to the nail by the touch pen 110 and transmit measured force information to the electronic device 120.

The electronic device 120 may receive the force information from the touch pen 110 and calculate a contact pressure between the finger and the sensor module 710 based on the received force information and pre-stored contact area information.

The electronic device 120 may generate pressure guide information 730 to guide change in contact pressure based on the calculated contact pressure and provide the pressure guide information 730 to the user through the display screen.

The electronic device 120 may measure a pulse wave of the user using the sensor module 710 of the electronic device 120. The electronic device 120 may measure the pulse wave of the user by using a part 720 of the display as a light source and using the sensor module 710 as a light receiver.

The electronic device 120 may estimate a blood pressure of the user based on the calculated contact pressure and the measured pulse wave.

Figure 8:
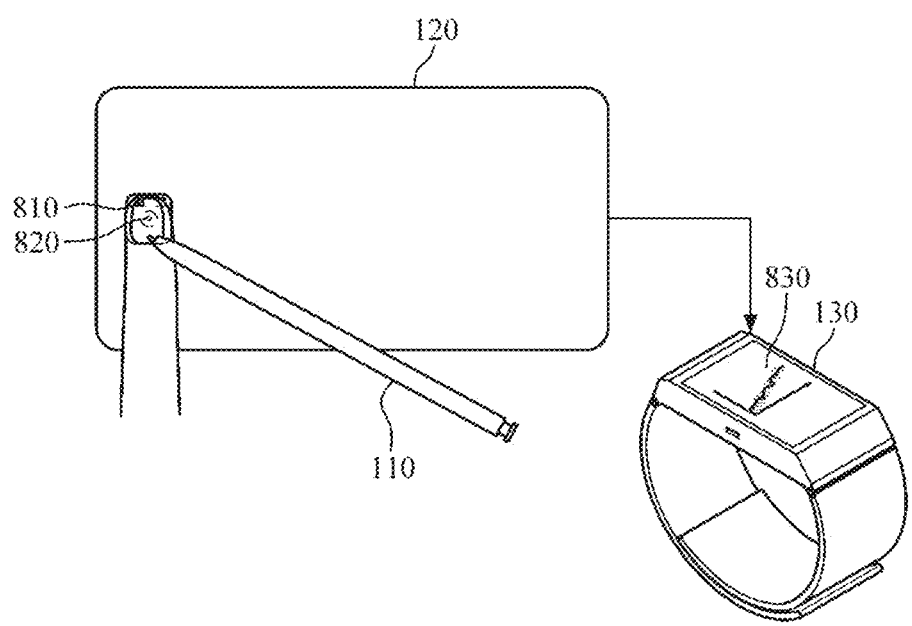
FIG. 8 is a diagram illustrating an example of measuring a blood pressure using the flash of a camera as a light source.

FIG. 8 is a diagram illustrating an example of measuring a blood pressure using the flash of a camera as a light source.

Referring to FIG. 8, a user may place his/her finger above a flash 810 of the electronic device 102 and a camera 820, place a touch pen 110 vertically above a nail and press the nail in a direction perpendicular to the electronic device 120. In this case, the electronic device 120 may provide the user with action guide information to guide a user's action to press the nail using the touch pen 110 through another electronic device 130 (e.g., a smart watch).

The touch pen 110 may measure a force applied to the nail by the touch pen 110 and transmit measured force information to the electronic device 120.

The electronic device 120 may receive the force information from the touch pen 110 and calculate a contact pressure between the finger and the camera 820 based on the received force information and pre-stored contact area information.

The electronic device 120 may generate pressure guide information 830 to guide change in contact pressure based on the calculated contact pressure and provide the pressure guide information 830 to the user through the other electronic device 130.

The electronic device 120 may measure a pulse wave of the user by using the flash 810 of the electronic device 120 as a light source and using the camera 820 as a light receiver. The electronic device 120 may estimate a blood pressure of the user based on the calculated contact pressure and the measured pulse wave.

Figure 9:
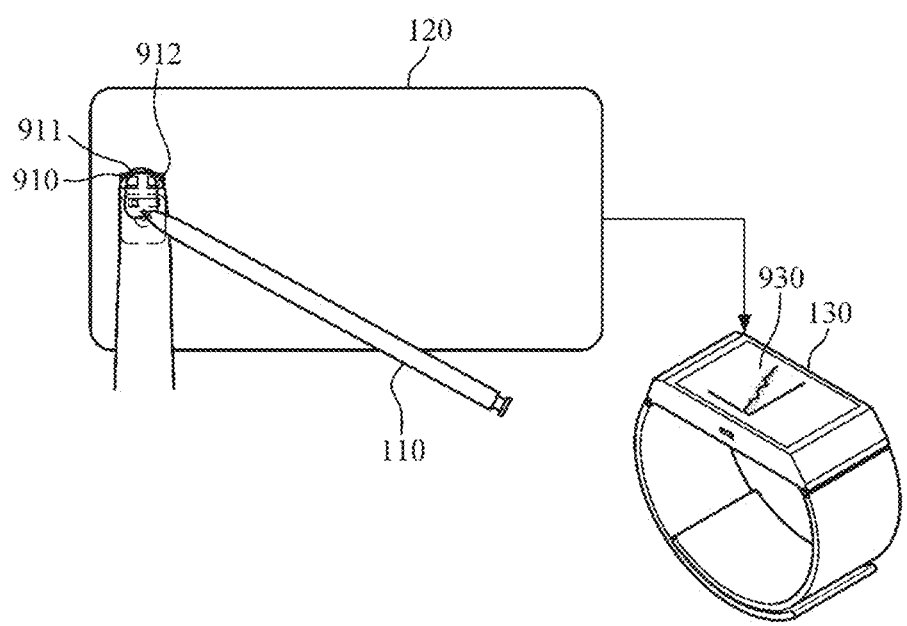
FIG. 9 is a diagram illustrating an example of measuring a blood pressure using a pulse wave sensor.

FIG. 9 is a diagram illustrating an example of measuring a blood pressure using a pulse wave sensor.

Referring to FIG. 9, a user may place his/her finger above a pulse wave sensor 910 of an electronic device 102, place a touch pen 110 vertically above a nail and press the nail in a direction perpendicular to the electronic device 120. The pulse wave sensor 910 may include a light source 911 and a light receiver 912.

According to one embodiment, the light source 911 may be formed as a light emitting diode (LED), a laser diode, or a fluorescent body and may emit visible light, NIR light, or MIR light. However, a wavelength of light emitted from the light source may vary depending on the measurement purpose or the component to be analyzed. In addition, the light source is not necessarily formed as a single light emitting body and may be formed as an array of a plurality of light emitting bodies. In addition, the light receiver 912 may be formed with a photodiode, a photo transistor (PTr), or a charge-coupled device (CCD) and may receive light reflected or scattered from an object of interest. The light receiver is not necessarily formed as a single element and may be formed as an array of a plurality of elements. The number and arrangement of the light sources and the light receiver may vary according to the application purpose of a pulse wave measurer 120 and the size and shape of the electronic device in which the pulse wave measurer 120 is mounted.

The electronic device 120 may provide action guide information to guide a user's action to press the nail using the touch pen 110 to the user through another electronic device 130 (e.g., a smart watch).

The touch pen 110 may measure a force applied to the nail by the touch pen 110 and transmit measured force information to the electronic device 120.

The electronic device 120 may receive the force information and calculate a contact pressure between the finger and the pulse wave sensor 910 based on the received force information and pre-stored contact area information.

The electronic device 120 may generate pressure guide information 930 to guide change in contact pressure based on the calculated contact pressure and provide the pressure guide information 930 to the user through the other electronic device 130.

The electronic device 120 may measure a pulse wave of the user using the pulse wave sensor 910. The electronic device 120 may estimate a blood pressure of the user based on the calculated contact pressure and the measured pulse wave.

Figure 10:
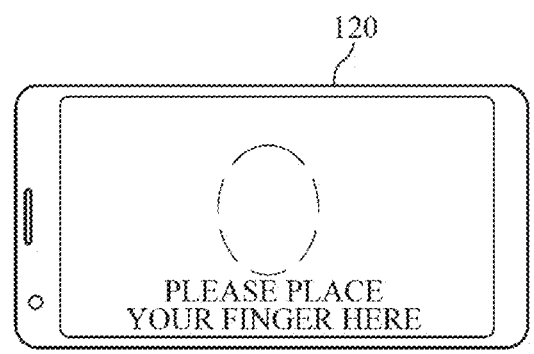
FIG. 10 is a diagram for describing a contact area measurement process.

FIG. 10 is a diagram for describing a contact area measurement process.

Referring to FIG. 10, the contact area measurement process may be performed such that a user's finger to be used for measuring a blood pressure is brought into contact with a display screen and the contact area is measured. In this case, there is no limitation on the number of times of contact, and when there are a number of times of contact, an average of the contact areas may be used. As illustrated, the electronic device 120 may provide area measurement guide information to the user through a display screen to guide the user's action so that the user's finger used to measure a blood pressure is brought into contact with the display screen to measure the contact area.

Figure 11:
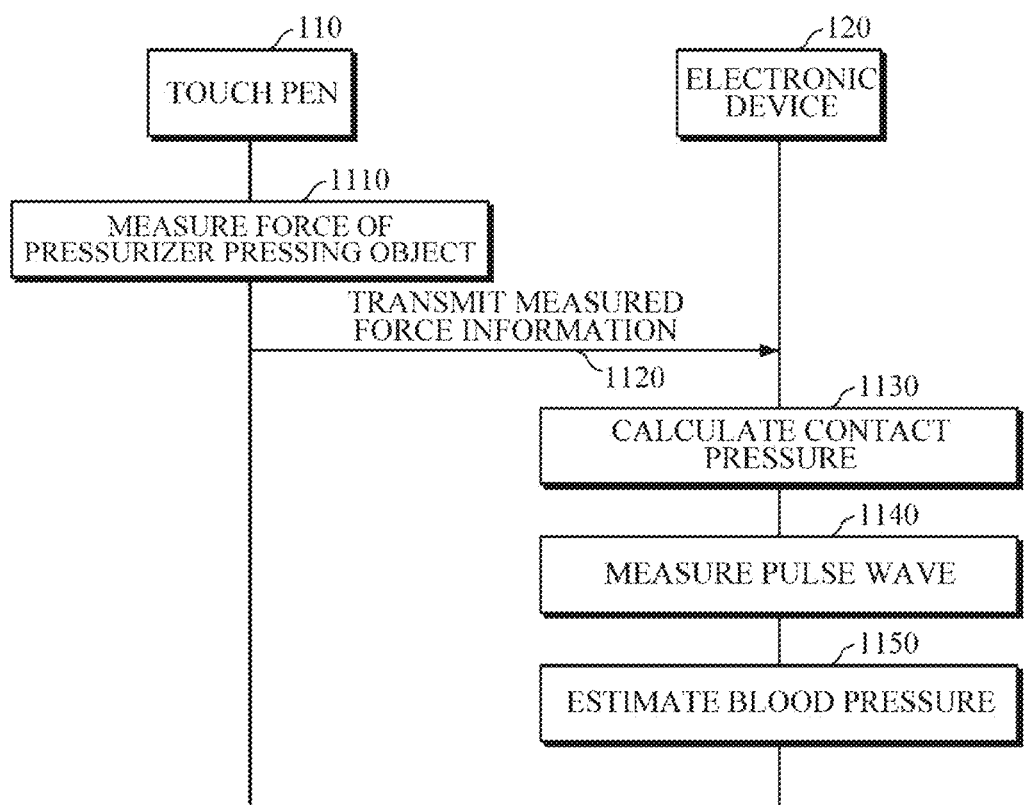
FIG. 11 is a flowchart illustrating a blood pressure measurement method according to one embodiment.

FIG. 11 is a flowchart illustrating a blood pressure measurement method according to one embodiment. The blood pressure measurement method of FIG. 11 may be performed by the blood pressure measurement system of FIG. 1.

Referring to FIG. 11, the touch pen 110 may measure a force of a pressurizer of the touch pen 110 pressing an object of interest in operation 1110.

The touch pen 110 may transmit measured force information to the electronic device 120 in operation 1120.

The electronic device 120 may receive the force information from the touch pen 110 and calculate a contact pressure between the object and the electronic device 120, which is caused by the force of the touch pen 110 pressing the object, based on the received force information in operation 1130. When the object is brought into contact with the sensor module as the touch pen 110 presses the object, the force of the touch pen 110 pressing the object may be transmitted to the sensor module of the electronic device 120 through the object. Therefore, according to one embodiment, the electronic device 120 may use the force information received from the touch pen 110, that is, the force information about the force of the pressurizer of the touch 110 pressing the object, as contact force information between the object and the sensor module of the electronic device 120 and calculate the contact pressure between the object and the sensor module based on the force information and pre-stored contact area information. In this case, the pre-stored contact area information may be a default value or a value measured in advance according to a contact area measurement process prior to measurement of a pulse wave of the object.

When the object is brought into contact with the sensor module of the electronic device 120 by the force of the touch pen 110 pressing the object, the electronic device 120 may measure a pulse wave of the object in operation 1140. According to one embodiment, the electronic device 120 may measure the pulse wave of the object using one of a face recognition sensor, a pulse wave sensor, a camera, an illuminance sensor, and an iris recognition sensor. For example, the electronic device 120 may measure the pulse wave of the object using a pulse wave sensor including a light source and a light receiver. In another example, the electronic device 120 may measure the pulse wave of the object by using natural light, a part or the whole of a display, a light source of the touch pen 110, or the flash of a camera as a light source and using one of the face recognition sensor, the camera, the illuminance sensor, and the iris recognition sensor as a light receiver.

The electronic device 120 may estimate a blood pressure of the object based on the pulse wave of the object and the contact pressure between the object and the electronic device 120 in operation 1150. For example, the electronic device 120 may estimate the blood pressure of the user by analyzing change in pulse wave in accordance with change in contact pressure.

Figure 12:
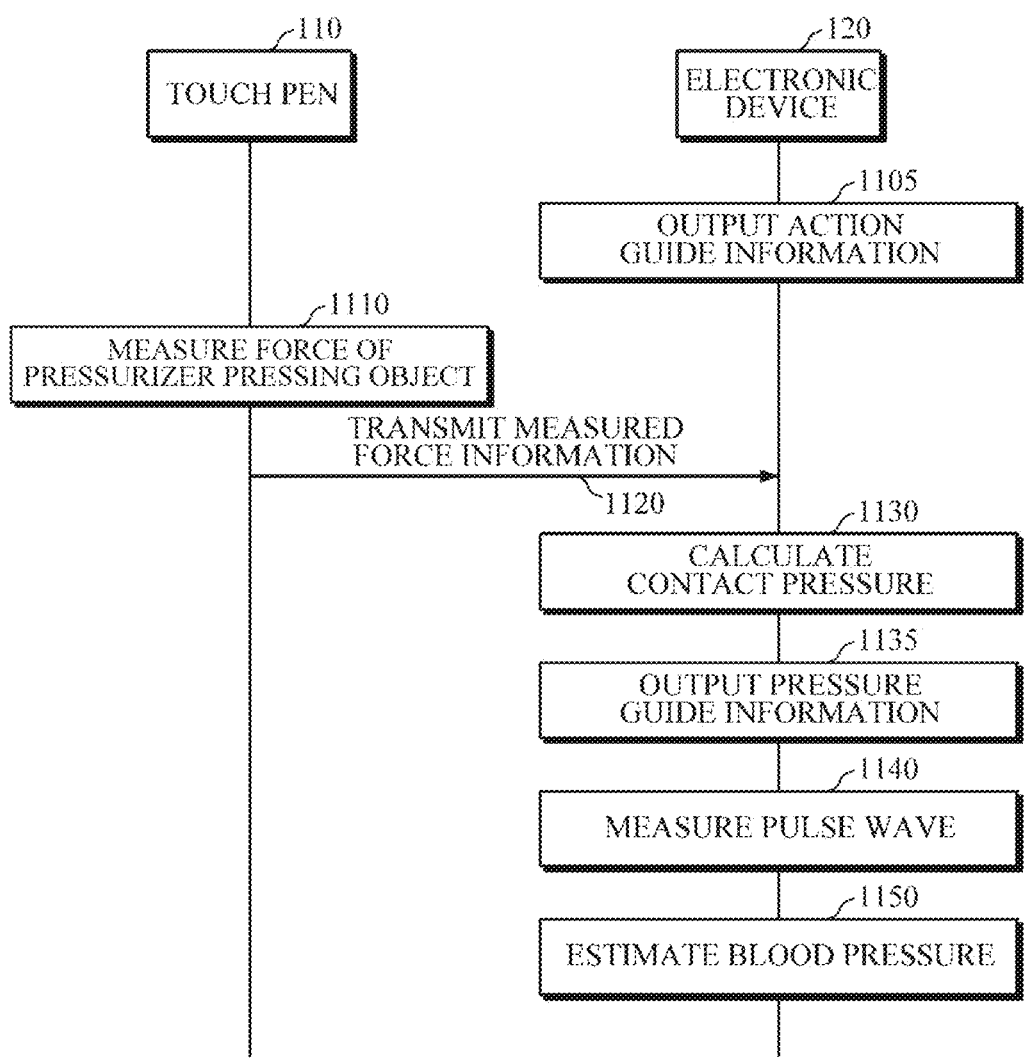
FIG. 12 is a flowchart illustrating a blood pressure measurement method according to another embodiment.

FIG. 12 is a flowchart illustrating a blood pressure measurement method according to another embodiment. The blood pressure measurement method of FIG. 12 may be performed by the blood pressure measurement system of FIG. 1. Operations 1110, 1120, 1130, 1140, and 1150 of FIG. 12 are the same as those described with reference to FIG. 11, and thus detailed descriptions thereof will not be reiterated.

In operation 1105, periodically or upon the occurrence of a specific event, such as a user command, an electronic device 120 may display or output action guide information to guide a user's action through a display or another electronic device so that a pulse wave of the object can be measured by applying a force to the object with the touch pen 110.

In operation 1135, the electronic device 120 may output pressure guide information through the display or another electronic device to guide change in contact pressure between the object and the electronic device 120 which is caused by a force of the touch pen 110 pressing the object.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:
1. An electronic device comprising:
 a communication interface configured to wirelessly receive, from a touch pen, force information about a force of the touch pen exerted onto an object against a contact surface of an optical sensor when the object is placed between the touch pen and the contact surface of the optical sensor;

the optical sensor configured to measure a pulse wave of the object when the object is brought into contact with the contact surface of the optical sensor by the force of the touch pen; and a processor configured to estimate a blood pressure of the object based on the force information and the pulse wave.

2. The electronic device of claim 1, wherein the optical sensor comprises at least one of a face recognition sensor, a pulse wave sensor, a camera, an illuminance sensor, and an iris recognition sensor.

3. The electronic device of claim 2, wherein the optical sensor is further configured to measure the pulse wave of the object by using at least one of natural light, a display of the electronic device, a light source of the touch pen, or a flash of the electronic device, as a light source of the optical sensor and by using the at least one of the face recognition sensor, the camera, the illuminance sensor, and the iris recognition sensor, as a light receiver of the optical sensor.

4. The electronic device of claim 2, wherein the pulse wave sensor comprises a light source configured to emit light to the object and a light receiver configured to receive light reflected or scattered from the object.

5. The electronic device of claim 1, wherein the communication interface is further configured to receive the force information from the touch pen that generates an electromagnetic field.

6. The electronic device of claim 1, wherein the communication interface is further configured to receive the force information from the touch pen using one of Bluetooth communication, Bluetooth low energy (BLE) communication, near field communication (NFC), wireless local access network (WLAN) communication, ZigBee communication, infrared data association (IrDA) communication, Wi-Fi direct (WFD) communication, ultra-wideband (UWB) communication, Wi-Fi communication, radio frequency identification (RFID) communication, third generation (3G) communication, fourth generation (4G) communication, and fifth generation (5G) communication.

7. The electronic device of claim 1, wherein the processor is further configured to calculate a contact pressure between the object and the electronic device, which is caused by the force of the touch pen pressing the object, based on the force information, and estimate the blood pressure of the object using the contact pressure and the pulse wave.

8. The electronic device of claim 7, wherein the processor is further configured to calculate the contact pressure between the object and the electronic device based on the force information and pre-stored contact area information indicating an contact area between the object and the electronic device.

9. The electronic device of claim 8, wherein the pre-stored contact area information is a default value.

10. The electronic device of claim 9, wherein the predetermined contact area measurement process comprises measuring the contact area when the object is brought into contact with a display screen of the electronic device.

11. The electronic device of claim 1, further comprising a power supply configured to supply power to the touch pen that generates an electromagnetic field.

12. The electronic device of claim 1, wherein the object is a body part of a user of the electronic device, and
wherein the processor is further configured to generate guide information for measuring the pulse wave of the object using the touch pen and provide the guide information to the user.

13. The electronic device of claim 12, wherein the guide information includes at least one of action guide information to guide the user to press the object against the electronic device by using the touch pen, and pressure guide information to guide change in contact pressure between the object and the electronic device which is caused by the force of the touch pen pressing the object.

14. The electronic device of claim 12, wherein the processor is further configured to provide the guide information through a display of the electronic device or through another electronic device.

15. A blood pressure measurement method implemented by an electronic device, the blood pressure measurement method comprising:
wirelessly receiving, from a touch pen, force information about a force of the touch pen exerted onto an object against a contact surface of an optical sensor when the object is placed between the touch pen and the contact surface of the optical sensor;
measuring a pulse wave of the object by using the optical sensor when the object is brought into contact with the contact surface of the optical sensor by the force of the touch pen; and
estimating a blood pressure of the object based on the force information and the pulse wave.

16. The blood pressure measurement method of claim 15, wherein the optical sensor comprises at least one of a face recognition sensor, a camera, an illuminance sensor, and an iris recognition sensor.

17. The blood pressure measurement method of claim 16, wherein the measuring the pulse wave of the object comprises measuring the pulse wave of the object by using natural light, a display of the electronic device, a light source of the touch pen, or a flash of the electronic device, as a light source of the optical sensor, and by using the at least one of the face recognition sensor, the camera, the illuminance sensor, and the iris recognition sensor, as a light receiver of the optical sensor.

18. The blood pressure measurement method of claim 15, wherein the estimating the blood pressure of the object comprises calculating a contact pressure between the object and the electronic device, which is caused by the force of the touch pen pressing the object, based on the force information, and estimating the blood pressure of the object based on the contact pressure and the pulse wave.

19. The blood pressure measurement method of claim 18, wherein the calculating the contact pressure comprises calculating the contact pressure between the object and the electronic device based on the force information and pre-stored contact area information indicating a contact area between the object and the electronic device.

20. The blood pressure measurement method of claim 19, wherein the pre-stored contact area is a default value.

21. The blood pressure measurement method of claim 15, wherein the object is a body part of a user of the electronic device, and
wherein the blood pressure measurement method further comprises generating action guide information to guide the user to press the object against the electronic device by using the touch pen, and providing the action guide information to the user.

22. The blood pressure measurement method of claim 15, further comprising generating pressure guide information to guide change in contact pressure between the object and the electronic device, which is caused by the force of the touch pen pressing the object.

\* \* \* \* \*